US009769166B1

(12) United States Patent
Lai et al.

(10) Patent No.: US 9,769,166 B1
(45) Date of Patent: Sep. 19, 2017

(54) WEARABLE SENSOR BASED SYSTEM FOR PERSON IDENTIFICATION (71) Applicant: International Business Machines Corporation, Armonk, NY (US)

(72) Inventors: Jui-Hsin Lai, White Plains, NY (US); Lifeng Nai, Atlanta, GA (US); Toyotaro Suzumara, New York, NY (US); Yinglong Xia, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/297,825

(22) Filed: Oct. 19, 2016

(51) Int. Cl.
*H04L 29/06* (2006.01)
*H04W 12/06* (2009.01)
*G06F 15/16* (2006.01)
*H04W 12/08* (2009.01)

(52) U.S. Cl.
CPC ........ *H04L 63/0861* (2013.01); *H04L 63/083* (2013.01); *H04L 63/0853* (2013.01); *H04W 12/06* (2013.01); *H04W 12/08* (2013.01)

(58) Field of Classification Search
CPC ............... H04L 63/0861; H04L 63/083; H04L 63/0853; H04W 12/06; H04W 12/08
See application file for complete search history.

(56) References Cited

U.S. PATENT DOCUMENTS 9,519,771 B2* 12/2016 Fadell ................... G06F 21/316
9,600,069 B2* 3/2017 Publicover .............. G06F 3/013
2004/0101212 A1* 5/2004 Fedorovskaya ... G06F 17/30265
    382/305
2009/0292724 A1* 11/2009 Jung ........................ A61B 5/16
2010/0033303 A1* 2/2010 Dugan ................. A61B 5/0002
    340/5.82

(Continued)

OTHER PUBLICATIONS

Irfan A. Essa, Alex P. Pentland: "Facial expression recognition using a dynamic model and motion energy", 1995, IEEE, pp. 360-367.*

(Continued)

*Primary Examiner* — Catherine Thiaw
(74) *Attorney, Agent, or Firm* — Scully, Scott, Murphy & Presser, P.C.; Daniel P. Morris, Esq.

(57) ABSTRACT

A system, method and computer program product for real-time recognition of individuals. The method comprises: receiving at a hardware processor, a first sensor data associated with the individual. The first sensor data associated with the individual is processed to determine an activity the individual is currently engaged in. Additionally, a second sensor data associated with the individual is received and processed to determine a feature associated with a muscle of said individual while engaged in activity. Based on the received sensor data and determined activity and muscle features, the method generates a model that correlates determined activities and corresponding muscle features of the individual user with the individual's identity. The model is subsequently used to identify the individual. By receiving and inputting real-time, sensor data from an individual into said generated model, the model generates and determines: an activity and a muscle feature for use in identifying the individual.

20 Claims, 5 Drawing Sheets

(56) References Cited

U.S. PATENT DOCUMENTS

| | | | |
|---|---|---|---|
| 2010/0172567 A1* | 7/2010 | Prokoski | A61B 5/0064 382/132 |
| 2011/0235870 A1* | 9/2011 | Ichikawa | G06F 21/32 382/118 |
| 2012/0007713 A1* | 1/2012 | Nasiri | G06F 1/1694 340/5.81 |
| 2014/0148709 A1* | 5/2014 | Gu | A61B 5/024 600/479 |
| 2014/0240103 A1 | 8/2014 | Lake et al. | |
| 2015/0151198 A1 | 6/2015 | Dugan et al. | |
| 2015/0242605 A1* | 8/2015 | Du | G06F 21/32 726/7 |
| 2016/0136429 A1 | 5/2016 | Massoumi et al. | |
| 2016/0301691 A1* | 10/2016 | Miller | G01S 5/08 |
| 2016/0361020 A1* | 12/2016 | LeBoeuf | A61B 5/7239 |

OTHER PUBLICATIONS

Fletcher et al., "Wearable Sensor Platform and Mobile Application for Use in Cognitive Behavioral Therapy for Drug Addiction and PTSD", 33rd Annual International Conference of the IEEE EMBS, Boston, MA, Aug. 30-Sep. 3, 2011, pp. 1802-1805.

Mohiuddin et al., "A multi-state model to improve the design of an automated system to monitor the activity patterns of patients with bipolar disorder", Journal of the Operational Research Society (2013) 64, May 2013, pp. 372-383.

Pei et al., "Human Behavior Cognition Using Smartphone Sensors", Sensors 2013, 13, ISSN 1424-8220, www.mdpi.com/journal/sensors, Jan. 2013, pp. 1402-1424.

Marschollek et al., "Sensors vs. experts—A performance comparison of sensor-based fall risk assessment vs. conventional assessment in a sample of geriatric patients", BMC Medical Informatics and Decisional Making 2011, 11:48, Jun. 28, 2011; pp. 1-7.

Anonymous, "Body location guidance using somatosensory feedback", IP.com Prior Art Database Technical Disclosure, IPCOM000190588D, Dec. 7, 2009.

Lindsay et al., "Improved Wearable Sensor Systems", IP.com Prior Art Database Technical Disclosure, IPCOM000030041D, Jul. 23, 2004.

* cited by examiner

WEARABLE SENSOR BASED SYSTEM FOR PERSON IDENTIFICATION

FIELD

The present disclosure generally relates to identification systems, and more particularly to a person identification system that identifies a person based on collaborative information from multiple wearable sensors.

BACKGROUND

The currently exists many modalities of personal identification systems. Current technologies include use of biometrics, e.g., fingerprints: automated fingerprint identification systems, self-authenticating identification card with fingerprint identification. Additional biometric data for use in personal identification include facial recognition: facial recognition system for security access and identification; use of face recognition for identification.

However, it is the case that use of ID cards, fingerprints, are inconvenient and insecure. Moreover, existing facial recognition systems are error prone.

While a wearable sensor platform and mobile application exist for use in cognitive behavioral therapy (e.g. healthcare and sports) such system a wearable sensor platform is not customized for person identification/recognition.

SUMMARY

Mobile devices, such as smart watches, are employed to collect and preprocess data from multiple types of wearable sensors provided on an individual. Accelerometer sensors of various body positions are used to collect activity information, which is processed to train machine learning model to classify personal activity modes, such as walking, running, and sleeping.

In one aspect, data from multiple muscle sensors are collected to extract muscle action features. The activity modes and muscle features are processed in a collaborative way to identify an individual person.

According to an aspect of the present disclosure, there is provided a method for recognizing individuals. The method comprises: receiving at a hardware processor, a first sensor data associated with the individual processing, by the hardware processor, the first sensor data associated with the individual to determine an activity the individual is currently engaged in; receiving at a hardware processor, a second sensor data associated with the individual; processing, by the hardware processor, the second sensor data associated with the individual to determine a feature associated with a muscle of the individual used while engaged in the determined activity; and generating a model that correlates determined activities and corresponding muscle features of the individual user with an identity of the individual.

According to another aspect of the present disclosure, there is provided a system for recognizing individuals. The system comprises: one or more sensor devices attached to and associated with an individual, each sensor data providing sensor data; a processing unit configured to receive the sensor data and store the sensor data in an associated memory storage device; the processing unit further configured to: receive a first sensor data associated with the individual; process said first sensor data associated with the individual to determine an activity the individual is currently engaged in; receive a second sensor data associated with the individual; process said second sensor data associated with the individual to determine a feature associated with a muscle of said individual while engaged in the determined activity; and generate a model that correlates determined activities and corresponding muscle features of the individual user with an identity of said individual.

According to yet another aspect of the present disclosure, there is provided a computer program product for performing operations. The computer program product includes a storage medium readable by a processing circuit and storing instructions run by the processing circuit for running a method. The method is the same as listed above.

DETAILED DESCRIPTION

As stated above, the present disclosure relates to identification systems, and more particularly to a person identification system that identifies a person based on collaborative information from multiple wearable sensors.

Figure 1:
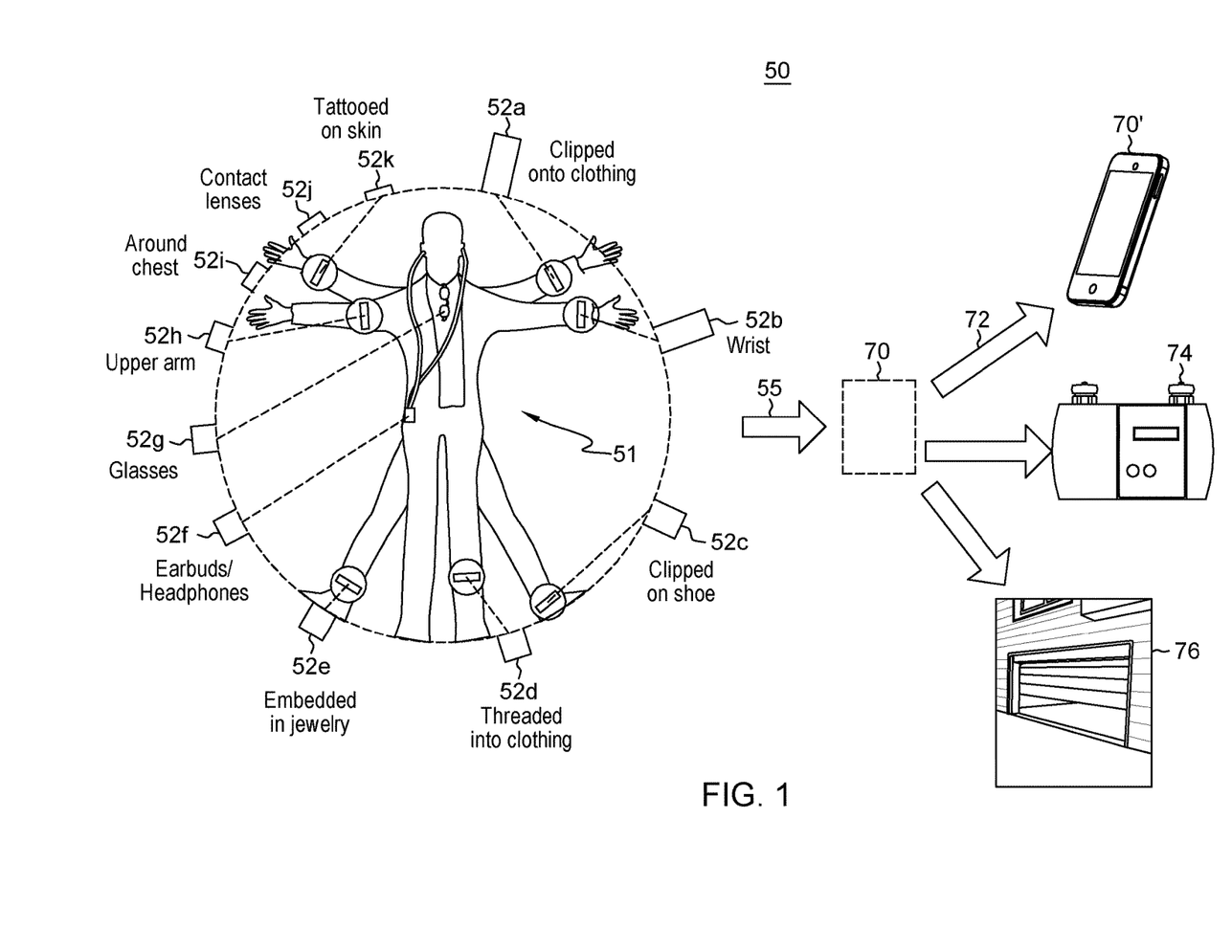
FIG. 1 shows a system diagram of personal identification system based on a multiple wearable sensor platform.

FIG. 1 shows a diagram of personal identification system 50 based on a wearable, multiple sensor platform. Such personal identification system based on a wearable multiple sensor platform provides for an accurate, secure and convenient identification system In the embodiment depicted, an individual or user 51 is shown having multiple "on body" sensors 52a, 12b, . . . , 52k that provide sensor data to a collection module that may preprocess the sensor data received. Such sensors may include but are not limited to: sensors attached to the body by any known means for sensing physiological and movement data for monitoring a user's physiological status: pressure sensors, temperature sensors, breath sensors, accelerometer(s), muscle sensor(s), hear rate sensor, EEG sensors, relaxation sensors (e.g., sensors for measuring depth, chest/stomach location and/or pace of breath) and other physiological measures such as include heart rate, respiratory rate, blood pressure, and muscle activity. For example, in non-limiting embodiments, muscle sensors such as an electrical based electromyography (EMG) sensor may be worn by individual. Data from such sensors may be used to positively identify the user or individual. For example, as shown in FIG. 1, a sensor 52a can be clipped to part of the user's clothing fabric; a sensor 52b can be embedded and operational as part of a watch worn on the user's wrist; a sensor 52c can be clipped to part of a user's shoe; a sensor 52d may be embedded into a piece of clothing; a sensor 52e may be embedded in a piece of jewelry worn by the user; a sensor 52f may be embedded in a user's headphone or earbuds worn by the user; a sensor 52g may be part of the user's eye glasses; a sensor 52h may be worn by the user in that user's upper arm; a sensor 52i may be worn around the chest of the user; a sensor 52*j* may be worn by the user, e.g., as part of a user's contact lens; and a sensor 52*k* may be worn by the user as part of a tattoo worn on the user's skin.

In one embodiment, the sensors are configured to include or interface with a wireless communication capability to transmit the user's sensed sensor data 55 in real-time to a mobile phone or like data processing device 70 configured to receive the user's sensor data and equipped with a model configured to identify or perform real-time recognition of the user based on the received sensor data. In a further embodiment, the device 70 includes capability to further use the authorization based on the recognized user, as a basis to allow the user to access that device 70 or open/use an application running on the device 70. In a further embodiment, the device 70 functions as an access point and includes communications capability to further relay a signal 72 representing a positive identification or recognition of the user to a further remote device or system (not shown) to initiate any responsive action, e.g., open up an application, based on the determined identification.

In one embodiment, the access point 70 may be a smartphone or a smartwatch device equipped with communications receiver for receiving the sensed data in real-time and storing the received data in a local memory. An application running at the access point device, e.g., smartphone or smartwatch, accesses a learned recognition model running on the device and invokes the recognition model for automatically identifying/recognizing the user based on the real-time sensor data received.

The model has been prior trained by machine learning on multiple wearable sensors, e.g., including the accelerometer and muscle sensors, worn on the user. Based on the recognition, the smartphone or smartwatch device may generate signal 72 to take or initiate a responsive action at that device, e.g., open up a software application on the same or different smartphone or smartwatch device 70'; access a secure website or Internet location; control or switch on a remote device 74; unlock or open a door of a user's home/garage 76. Thus, the responsive action may be related to an activity the user is currently engaged in, e.g., enter a password to access an application, open a garage door from a remote device on a user's car, etc.

In one embodiment, the built identity recognition model may reside on and run in an operating device or system in which the user may subsequently be required to be identified in order to conduct an action, e.g., enter a password to open an application, at that device or system.

In a further embodiment, besides the use of a smartphone or smartwatch device 70 as an access point, there may alternately be employed a wearable electronic processor embedded in an article of clothing that can be worn or attached to a user (e.g., carried in a container, purse, ring, or wallet, or in some other object near the user) and serves to function as a centralized processing "hub" associated with the user or individual. This hub may be a configuration that receives information from the one or more sensors 52A, . . . , 52K and then sends information about and/or the sensor data to a remote computer or data storage device, optionally after performing a preprocessing of the data at the central hub. For example, a wireless signal 72 may be sent to another computing device (not shown), and/or can write the information into a memory that can later be downloaded to a computer, e.g., for user recognition model training/ analysis.

Referring to FIG. 1, in one embodiment, a user wears a minimum of one or more of a variety of sensors 52*a*, 52*b*, . . . , 52*k* such as shown in FIG. 1 including, but not limited to: an accelerometer and muscle activity sensors which may provide sensor data to a computer system via a communications interface. Via such interface, a user may further enter further information such as the user's identification. The sensor data and other information entered by the user is stored and used to build, using machine learning, a model for use in personal identification/recognition.

Figure 2:
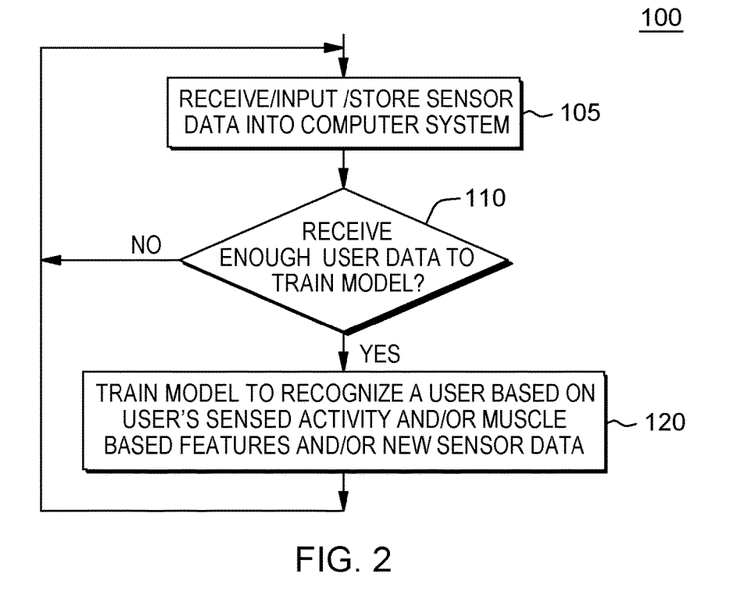
FIG. 2 depicts a software block diagram of a method depicting the development and use of the model for personal recognition or identification.

FIG. 2 depicts a software block diagram of a method 100 depicting the development and use of the model for personal recognition or identification. The method includes at 105 the receiving and collecting of sensor data from an individual, e.g., when engaging in an activity. Given the received sensor data from a user engaged in an activity, for example, for one or more of the embedded and/or worn sensor devices 52*a*-52*j*, features of the received sensor data signals may be extracted for correlation with a particular user identity. Such extracted data may include the activity sensor data and muscle feature data. Such aspects may include a frequency measure or detecting signature pattern(s) in the received sensor data signal(s). The sensor data collected may be stored in one or more memory storage devices, e.g., making up database (not shown) and this data is accessed via a local network, e.g., private or public network via a network input/output interface for use by the hardware processor in building/applying the recognition model.

Figure 5:
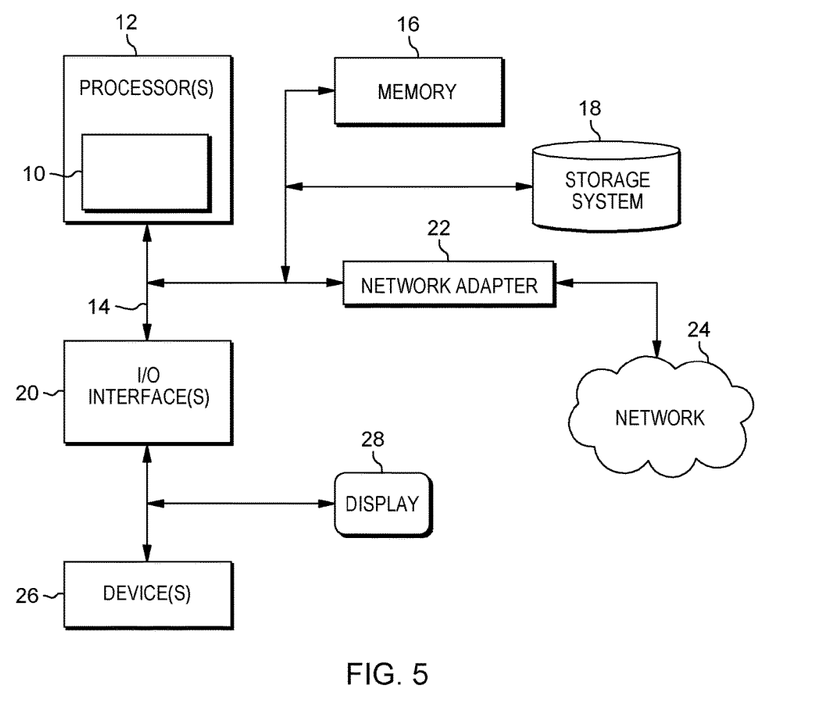
FIG. 5 depicts an exemplary hardware configuration for performing methods such as described herein.

In one embodiment, the sensor data is provided to a computing system 10 such as shown in FIG. 5 that includes one or more servers comprising machine learning applications and database software components for building the model for personal recognition or identification. Received user profile data is additionally stored in a memory storage device, e.g., a database, for association with that user's particular identification and may be used in an off-line process for training the recognition model.

In one embodiment, the user may be queried to enter, e.g., via a access point device interface, that user's profile information, e.g., the user identification and/or other user profile data, e.g., the user's gender (male/female), age, marital status and/or any other data point that might be used for training a system for user recognition/identification.

An initial determination is thus made at 110 as to whether there is enough sensor signal data received or available to accurately train the recognition model. If it is determined at 110, there is not enough training data to accurately train the model for use in identifying the user, the process returns to 105 to receive additional sensor data for use in training the recognition model. For example, sensed data for learning may include muscle sensor data from key user muscle systems, e.g., chest, legs, arms, heart and stomach.

The steps 105-110 iterate until it is determined that there is a sufficient amount of sensor data collected for training the model to detect a particular activity that is used to identify the user. Once at 110 there is enough data, at 120, the model is trained to recognize a user based on a user's sensed activity and/or muscle based features. In one embodiment, a neural network program implementing well-known algorithms known to skilled artisans, may be trained over time to estimate or approximate functions based on key features of the extracted sensor data that can be used for identifying the user. It is understood that the training of the neural network model may occur offline and that the model build may be continuously refined. Thus, from 120, the process returns to 105 as shown as new sensor data is received for that user engaging in an activity to be used to identify the user. In one embodiment, the model may be continually trained to recognize additional activities and corresponding muscle features and be refined as new/additional better sensors become available or are implemented.

Figure 3A:
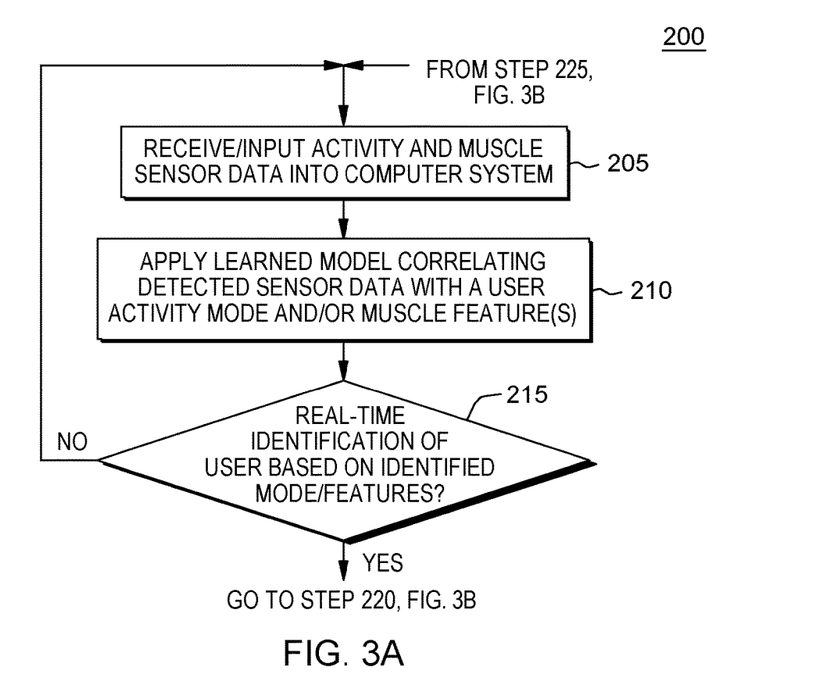
FIG. 3A-3B depicts steps of using an identity recognition model for recognizing a user based on that user's sensed activity and muscle features.
Figure 3B:
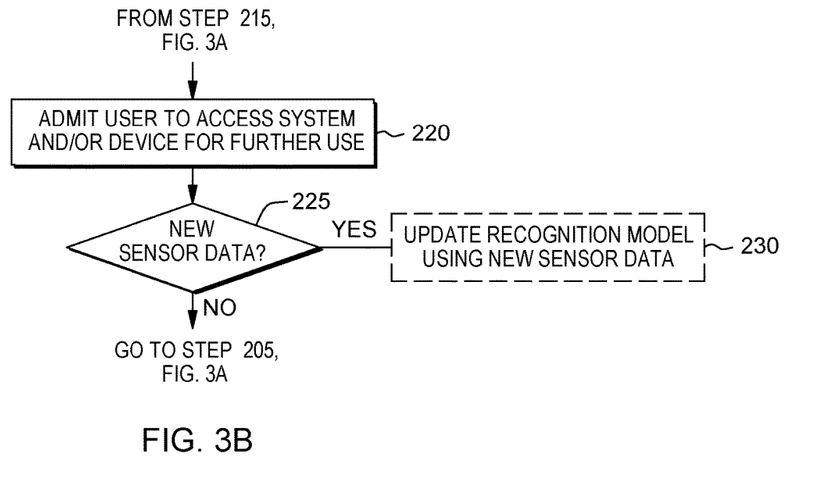

FIG. 3A-3B depicts steps of using the built identity recognition model in real-time for recognizing a user based on that user's sensed activity and muscle features. In one embodiment, the built model may reside on and run in an operating environment or system in which the user may subsequently be required to be identified in order to conduct an action, e.g., enter a password to open an application.

FIG. 3A depicts a software block diagram of a method 200 for real-time use of the machine learned model for personal recognition or identification. The method includes, the real-time receipt of sensor data from one or more devices as shown in FIG. 1 at a centralized device, e.g., a user's smartphone or smartwatch or processing hub, at 205. The real-time receiving and collecting of sensor data from an individual attempting to engage in an activity, e.g., operate the user's smartphone or smartwatch or an application running on the user's smartphone or smartwatch. In other embodiments, the activity may comprise a user using a device, e.g., a remote switch device for automatically opening up a door such as a garage door. In one embodiment, the received sensor data is input into the model and at 210, the learned model is applied for correlating detected sensor data with a user activity mode and/or muscle feature(s). At 215 a determination is made as to whether the user's identification is verified based on detected activity mode/muscle features obtained from the real-time sensor data. If the user's identity is not verified, the method returns to 205 in order to receive additional real-time sensor data sufficient so that the model can determine with reasonable certainty that the received data correlates with the particular user.

Otherwise, at 215, if it is determined that detected activity mode/muscle features obtained from the real-time sensor data does identify the user to a degree of certainty, then the process continues to step 220, FIG. 3B where, upon user verification, the process running the model can trigger the particular system or device or application to admit and/or grant access for the user as the user has been positively identified. In one embodiment, an additional determination may be made at 225 to determine whether any of the received data constitutes new sensor data, e.g., a new or replaced sensor or new data that may be associated with a new user activity mode or a new muscle feature associated with a new activity that may require further training of the user recognition model. For example, it is conceivable that a user's activity changes or muscle features change when engaging in a recognized activity. Thus, the system will continuously feedback new sensor data in order to further train the model to recognize new user activity mode and/or muscle features and prevent a loss of model accuracy over time.

If at 225, it is determined that the received data included new sensor data, e.g., then the process proceeds to 230 for updating the recognition neural network model based on the new activity mode or muscle feature. The model updating may occur immediately after user recognition or subsequently in an off-line process. If at 225, there is no new user activity sensor data or muscle features data, then the process proceeds back to 205, FIG. 3A for subsequent use/training.

Figure 4:
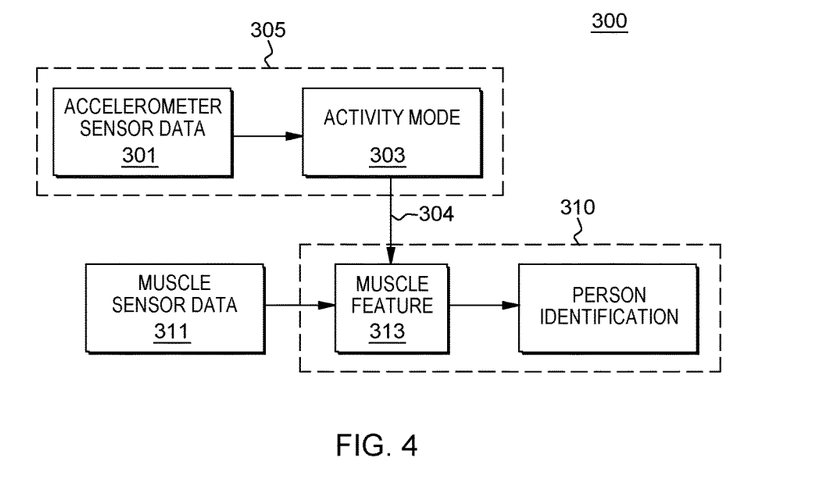
FIG. 4 depicts a method for training the neural network recognition model for subsequent use in real-time positive user identification.

FIG. 4 depicts a method 300 for training the neural network recognition model and for subsequent use in using the neural network recognition model for real-time positive user identification. The training method includes an activity learning aspect 305 and an identity learning aspect 310. First, in activity learning 305, the received and/or collected activity data from the user includes accelerometer sensor data 301 that is used to identify the activity, i.e., activity mode 303, that user is engaging in. Further, in the identity learning aspect 310, the received and/or collected activity data includes muscle sensor data 311 for evaluation in a muscle feature detecting function 313. Based on the learned activity mode the user is engaging in, the muscle behavior of the person may be different (depending on activity). Thus, the activity mode information from activity learning 305 is input as an additional parameter 304 to the muscle feature detecting function 313. The muscle feature detecting function 313 thus uses concurrently received muscle sensor data 311 and activity mode parameter 304 to correlate and associate the activity, e.g., walking, running, sitting idle, sleeping, driving, etc. and muscle features with that user's identity at 320.

FIG. 4 further depicts the subsequent use of the neural network recognition model for real-time positive user identification such as performed at step 213, FIG. 3A, and which is similar to the training/learning aspect. For example, returning to step 310, FIG. 3A, in applying the learned identity recognition model in real-time, the detected muscle feature sensor data received from the user in conjunction with the received activity mode parameter 304 (determined based on received accelerometer sensor data from that user) are used to collaboratively determine a user's muscle feature(s) for positive correlation with a person's identity at 320.

As an example, types of activities that can be monitored by collecting sensor data includes but is not limited to: walking, running, sitting idle, sleeping, driving. For example, while engaged in such of these activities, a user may desire to perform a further action such as activate a cell phone, or automatically generate a password to open an application running on a smart watch or smart phone, or open up a door, unlock a security feature on a device and/or remotely control a device. For each of these further actions, a user authorization is required. Thus, using the trained model, the activity mode that user is engaged in, and the particular muscle features sensed while engaging in that activity are used to uniquely identify the person. The sensed data is a replacement for a biometric data such as a finger print, and the present system and method can be used in any application that may require identity recognition.

FIG. 5 illustrates a schematic of an example computer or processing system that is configured to run the learned identify recognition model and assist in the real-time identification of a user based on that user's sensed activity and muscle features in the embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 5 may include, but are not limited to, personal computer systems, server computer systems, thin clients, thick clients, wrist, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system.

Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 10 that performs the model build and model use methods described herein. In one embodiment, a neural network framework module 10 having instructions employing the methods herein may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, and external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only, and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An identity recognition system comprising:
one or more accelerometer sensor devices and muscle sensor devices attached to and associated with an individual engaged in a physical activity; and
at least one processor and a memory coupled to the at least one processor, wherein the memory comprises instructions which, when executed by the at least one processor, cause the at least one processor to:
receive, in real-time, a first sensor data from said one or more accelerometer devices attached to and associated with the individual;
receive, in real-time, a second sensor data from said muscle sensor devices attached to the individual's arm, leg, stomach or chest muscle groups exclusive of the cardiac muscle of the individual;
input said real-time first sensor data from said one or more accelerometer devices to a model trained to correlate said first sensor data to a learned physical activity engaged by the individual;
determine, using said trained model and said real-time first sensor data, the physical activity currently engaged in by the individual;
input said real-time second sensor data from said muscle sensor devices to said trained model;
detect, using said trained model, a muscle feature of the individual based on said real-time second sensor data from said muscle sensor devices and said determined physical activity the individual is currently engaged in,
wherein said model is trained to further correlate the determined physical activity currently engaged in by the individual and corresponding muscle features of the individual with an identity of said individual, and
use the trained model to identify the individual, in real-time based on the determined physical activity the individual is currently engaged in and detected muscle feature of the individual.

2. The identity recognition system of claim 1, wherein said individual is desirous of accessing or opening a device having said at least one processor with which said model is run, wherein responsive to said identifying the individual, said instructions, when executed by the at least one processor, further cause the at least one processor to:
    automatically activate the device to permit user access therein.
3. The identity recognition system of claim 1, wherein said individual is desirous of opening an application running on the device having said at least one processor with which said model is run, wherein responsive to said identifying the individual, said instructions, when executed by the at least one processor, further cause the at least one processor to:
    automatically activate the application running on the device to permit user access to the application.
4. The identity recognition system of claim 1, wherein said individual is desirous of activating a remote system or device from said individual, wherein responsive to said identifying the individual, said instructions, when executed by the at least one processor, further cause the at least one processor to:
    automatically initiate communication of a signal for use in activating and carrying out a function in the remote system or device.
5. The identify recognition system of claim 4, wherein the function carried out in the remote system or device is selected from the group consisting of:
    open up a software application on the remote system or device, access a secure web-site or Internet location, control or switch on a remote device, automatically unlock or open a door of the individual's residence.
6. The identity recognition system of claim 1, wherein responsive to said identifying the individual, said instructions, when executed by the at least one processor, further cause the at least one processor to:
    automatically generate a password associated with that individual for use in opening activating a device or activating an application running on the device.
7. The identity recognition system of claim 1, wherein said instructions, when executed by the at least one processor, further cause the at least one processor to:
    generate an activity mode parameter corresponding to the individual's determined physical activity; and
    use said activity mode parameter for determining said muscle feature of the individual's determined physical activity.
8. The identity recognition system of claim 1, wherein said instructions, when executed by the at least one processor, further cause the at least one processor to:
    use machine learning to train and update, based on received accelerometer sensor data, said model to classify an individual's physical activity, wherein the determined physical activity currently engaged in by the individual is selected from the group consisting of: walking, running, sitting idle, sleeping, driving a vehicle.
9. A method for recognizing individuals comprising:
    receiving, in real-time, at at least one hardware processor, a first sensor data from one or more accelerometer devices attached to and associated with an individual engaged in a physical activity;
    receiving, in real-time, at the at least one hardware processor, a second sensor data from one or more muscle sensor devices attached to the individual's arm, leg, stomach or chest muscle groups exclusive of the cardiac muscle of the individual;
    inputting, using said at least one hardware processor, said real-time first sensor data from said one or more accelerometer devices to a model trained to correlate said first sensor data to a learned physical activity engaged by the individual;
    determining, using said trained model and said real-time first sensor data, the physical activity currently engaged in by the individual;
    inputting, using said at least one hardware processor, said real-time second sensor data from said muscle sensor devices to said trained model;
    detecting, using said trained model, a muscle feature of the individual based on said real-time second sensor data from said muscle sensor devices and said determined physical activity the individual is currently engaged in, wherein said model is trained to further correlate the determined physical activity currently engaged in by the individual and corresponding muscle features of the individual with an identity of said individual, and
    using the trained model, at said least one hardware processor, to identify the individual in real-time, based on the determined physical activity the individual is currently engaged in and detected muscle feature of the individual.
10. The method of claim 9, wherein said individual is desirous of accessing or opening a device having said at least one hardware processor with which said model is run, wherein responsive to said identifying the individual, said method further comprises:
    automatically activating, using said at least one hardware processor, the device to permit user access therein.
11. The method of claim 9, wherein said individual is desirous of opening an application running on the device having said at least one hardware processor with which said model is run, wherein responsive to said identifying the individual, said method further comprises:
    automatically activating the application running on the device to permit user access to the application.
12. The method of claim 9, wherein said individual is desirous of activating a remote system or device from said individual, said method further comprising:
    responsive to said identifying the individual, automatically initiating communication of a signal for use in activating and carrying out a function in the remote system or device.
13. The method of claim 12, wherein the function carried out in the remote system or device is selected from the group consisting of:
    open up a software application on the remote system or device, access a secure web-site or Internet location, control or switch on a remote device, automatically unlock or open a door of the individual's residence.
14. The method of claim 9, further comprising:
    generating, using said at least one hardware processor, an activity mode parameter corresponding to the individual's determined physical activity; and
    using said activity mode parameter for determining said muscle feature of the individual's determined physical activity.
15. The method of claim 9, further comprising:
    using machine learning to train and update said model, at said at least one hardware processor, based on received accelerometer sensor data, to classify an individual's physical activity, wherein the determined physical activity currently engaged in by the individual is selected from the group consisting of: walking, running, sitting idle, sleeping, driving a vehicle.

16. A computer program product stored in a non-transitory computer-readable storage medium having computer readable program instructions, the computer readable program instructions read and carried out by at least one processor for performing a method for identity recognition, wherein the method comprises:
- receiving, in real-time, at at least one processor, a first sensor data from one or more accelerometer devices attached to and associated with an individual engaged in a physical activity;
- receiving, in real-time, at the at least one processor, a second sensor data from one or more muscle sensor devices attached to the individual's arm, leg, stomach or chest muscle groups exclusive of the cardiac muscle of the individual;
- inputting, using said at least one processor, said real-time first sensor data from said one or more accelerometer devices to a model trained to correlate said first sensor data to a learned physical activity engaged by the individual;
- determining, using said trained model and said real-time first sensor data, the physical activity currently engaged in by the individual;
- inputting, using said at least one processor, said real-time second sensor data from said muscle sensor devices to said trained model;
- detecting, using said trained model, a muscle feature of the individual based on said real-time second sensor data from said muscle sensor devices and said determined physical activity the individual is currently engaged in, wherein said model is trained to further correlate the determined physical activity currently engaged in by the individual and corresponding muscle features of the individual with an identity of said individual, and
- using the trained model, at said least one processor, to identify the individual in real-time, based on the determined physical activity the individual is currently engaged in and detected muscle feature of the individual.

17. The computer program product of claim 16, wherein said individual is desirous of accessing or opening a device having said at least one processor with which said model is run, or opening an application running on the device, wherein responsive to said identifying the individual, said method further comprises:
- automatically activating, using said at least one processor, the device to permit user access therein and/or automatically activating the application running on the device to permit user access to the application.

18. The computer program product of claim 16, wherein said individual is desirous of activating a remote system or device from said individual, said method further comprising:
- responsive to said identifying the individual, automatically initiating communication of a signal for use in activating and carrying out a function in the remote system or device.

19. The computer program product of claim 16, wherein said method further comprises:
- generating an activity mode parameter corresponding to the individual's determined physical activity; and
- using said activity mode parameter for determining said muscle feature of the individual's determined physical activity.

20. The computer program product of claim 16, wherein said method further comprises:
- using machine learning to train and update said model based on received accelerometer sensor data, to classify an individual's physical activity, wherein the a determined physical activity currently engaged in by the individual is selected from the group consisting of: walking, running, sitting idle, sleeping, driving a vehicle.

* * * * *

UNITED STATES PATENT AND TRADEMARK OFFICE
CERTIFICATE OF CORRECTION

| | | |
|---|---|---|
| PATENT NO. | : 9,769,166 B1 | Page 1 of 1 |
| APPLICATION NO. | : 15/297825 | |
| DATED | : September 19, 2017 | |
| INVENTOR(S) | : Jui-Hsin Lai et al. | |

It is certified that error appears in the above-identified patent and that said Letters Patent is hereby corrected as shown below:

On the Title Page

Item (72) Inventors should read:
Jui-Hsin Lai, White Plains, NY (US);
Lifeng Nai, Atlanta, GA (US);
Toyotaro Suzumura, New York, NY (US);
Yinglong Xia, Rye Brook, NY (US)

Signed and Sealed this
Twenty-eighth Day of February, 2023

Katherine Kelly Vidal
*Director of the United States Patent and Trademark Office*